United States Patent [19]

McMichael

[11] Patent Number: 4,880,626
[45] Date of Patent: Nov. 14, 1989

[54] IMMUNOTHERAPEUTIC METHODS AND COMPOSITIONS FOR THE TREATMENT OF DISEASES OF VIRAL ORIGIN, INCLUDING ACQUIRED IMMUNE DEFICIENCY SYNDROME

[76] Inventor: John McMichael, Westfall & Larry Hill Rd., R.D. 1, Delanson, N.Y. 12053

[21] Appl. No.: 86,372

[22] Filed: Aug. 17, 1987

Related U.S. Application Data

[63] Continuation-in-part of Ser. No. 692,822, Jan. 18, 1985, Pat. No. 4,692,332.

[51] Int. Cl.[4] .................... A61K 39/00; A61K 45/05; A61K 39/40
[52] U.S. Cl. .................................. 424/88; 424/119; 514/2
[58] Field of Search .................................. 424/88, 85

[56] References Cited

U.S. PATENT DOCUMENTS

| | | | |
|---|---|---|---|
| 3,883,499 | 5/1975 | Tachibana et al. | 530/855 |
| 4,002,738 | 1/1977 | Johnson et al. | 514/15 |
| 4,173,641 | 11/1979 | Kraska | 568/436 |
| 4,311,688 | 1/1982 | Burchiel et al. | 424/9 |
| 4,321,260 | 3/1982 | Auclair | 514/15 |
| 4,323,546 | 4/1982 | Crockford et al. | 436/547 |
| 4,395,394 | 7/1983 | Wolff et al. | 424/88 |
| 4,410,510 | 10/1983 | Livingston-Wheeler et al. | 424/92 |
| 4,520,113 | 5/1985 | Gallo et al. | 424/85 |
| 4,692,332 | 9/1987 | McMichael | 424/88 |
| 4,708,818 | 11/1987 | Montagnier et al. | 435/5 |
| 4,732,864 | 3/1988 | Tolman | 436/547 |

FOREIGN PATENT DOCUMENTS

| | | |
|---|---|---|
| 84046487 | 1/1984 | Japan . |
| 89190 | 4/1989 | Japan . |
| 86/04241 | 7/1986 | PCT Int'l Appl. . |

OTHER PUBLICATIONS

Acevedo, H. F. et al., *Infection & Immunity*, 31: 487-494 (1981).
Akiyama, M. et al., *Journal of Immunology*, 131:3085-3090 (1983).
Balint, J. et al., *Chem. Abstracts*, 100: 83936s (1984).
Bogdanov, I. G. et al., *Byulletin Eksperimental'noi Biologia i Meditsiiny*, 84: 709 (1977).
Bogdanov, I. G. et al., *FEBS Letters*, 57:259 (1975).
Burchiel, S. W. et al., *Chem. Abstracts*, 95:86351m (1981).
Cabradilla, C. D. et al., *Bio/Technology*, 4:128-133 (1986).
Chakrabarti, S. et al., *Nature*, 320: 535-537 (1986).
Chang, N. T. et al., *Nature*, 315:151-154 (1985).
Chang, T. W. et al., *Bio/Technology*, 3:905-909 (1985).
Chugai, *Chem. Abstracts*, 101:235588r (1984).
Cohen, J., *British Journal of Hospital Medicine*, 31:250-259 (1984).
Cohen, D. et al., *Chem. Abstracts*, 101:65664t (1984).
Cooper, P. D. et al., *Chem. Abstracts*, 100:84075x (1984).
Crockford, D. R. et al., *Chem. Abstracts*, 92:176610n (1980).
Crowl, R. et al., *Cell*, 41:979-986 (1985).
Franchini, G. et al., *Proc. Nat'l. Acad. Sci. U.S.A.*, 83:5282-5285 (1986).
Franklin, D., *Science News*, 126:261 (1984).
Gershon, R. K. et al., *J. Exp. Med.*, 153: 1533-1546 (1981).
Green, D. R. et al., *Ann. Rev. Immunol.*, 1:439-463 (1983).
Green, D. R., "Contrasuppression: Its Role in Immunoregulation", in *The Potential Role of T-Cells in Cancer Therapy*, Fefer et al., eds., Raven Press, New York (1982).
Herberman, R. B., Chapter 19 in *Immunology III* (Bellanti, ed.), W. B. Saunders Co., pp. 330-345 (1985).
Herscowitz, H. B., Chapter 7 in *Immunology III*, Bellanti, J. W. Saunders, Philadelphia, pp. 117-159 (1985).
Hlavayova, F. et al., *Chem. Abstracts*, 100:96263v (1984).
Hu, S. et al., *Nature*, 320:537-540 (1986).
Kellen, J. A. et al., *Cancer Immunol. Immunother.*, 13:2-4 (1982).
Kellen, J. A. et al., *AACR Abstracts*, 23:235 (Mar. 1982) (Abstract 928).
Kieny, M. P. et al., *Bio/Technology*, 4:790-795 (1986).
Klavins, J. V., *Annals of Clinical and Laboratory Science*, 13:275-280 (1983).
Knecht, M., *Chem. Abstracts*, 92:88377m (1980).
Kolsch, E., *Scand. J. Immunol.*, 19:387-393 (1984).
Langcone, J. J. et al., *Chem. Abstracts*, 101:88606q (1984).
Lewin, B., Chapter 13 in *Genes*, John Wiley & Sons, New York, pp. 202-216 (1983).
Liu, W. T. et al., *Chem. Abstracts*, 101:70689j (1984).
Liu, W. T. et al., *Chem. Abstracts*, 101:228353q (1984).
Loblay, R. H. et al., *Aust. J. Exp. Biol. Med. Sci.*, 62:11-25 (1984).
Luciw, P. A. et al., *Nature*, 312:760-763 (1984).

(List continued on next page.)

Primary Examiner—Ronald W. Griffin
Attorney, Agent, or Firm—Marshall, O'Toole, Gerstein, Murray & Bicknell

[57] ABSTRACT

Methods and compositions useful for treating acquired immune deficiency syndrome by once daily administration of substances characteristic of acquired immune deficiency syndrome-afflicted cell (such as human chorionic gonadotropin), and effective fragments and derivatives thereof, in a pharmaceutically effective amount less that the lowest amount necessary to provoke a humoral immune response, as exemplified by the existence of a negative wheal upon subcutaneous administration. Illustrative of such methods and compositions is the administration of a composition including human chorionic gonadotropin (HCG), a lysate of *Staphylococcus aureus*, influenza virus vaccine, and fractionated HIV virus, including peptide T.

10 Claims, No Drawings

OTHER PUBLICATIONS

Manzari, V. et al., *Surv. Immunol. Res.*, 1:122–125 (1982).
Melmed, S. et al., *Chem. Abstracts*, 99:689a (1983).
Miller, J. B., *Anals. of Allergy*, 42:295–305 (1979).
Miller, J. B., *Clinical Medicine*, 81:16–19 (1974).
Miller, J. B. et al., *J. of Med. Assoc. of Alabama*, 41:493 (1972).
Mitsui, *Chem. Abstracts*, 101:17331k (1984).
Miyakoshi, H. et al., *Chem. Abstracts*, 96:67127x (1982).
Morgan, M. A. et al., *Journal of Virology*, 46:177–186 (1983).
Muesing, M. A. et al., *Nature*, 313:450–458 (1985).
Papademetriou, V. et al., *Chem. Abstracts*, 96:15389q (1982).
Pert, C. B. et al., *Proc. Nat'l Acad. Sci. U.S.A.*, 83:9254–9258 (1986).
Putney, S. D. et al., *Science*, 234:1392–1395 (1986).
Ratner, L. et al., *Nature*, 313:277–284 (1985).
Reilly, D. T. et al., *Lancet*, II:881–886 (1986).
Sanchez-Pescador, R. et al., *Science*, 227:484–492 (1985).
Simon, W. E. et al., *J.N.C.I.*, 70:839–845 (1983).
Yamauchi, K. et al., *J. Exp. Med.*, 153:1547–1561 (1981).

IMMUNOTHERAPEUTIC METHODS AND COMPOSITIONS FOR THE TREATMENT OF DISEASES OF VIRAL ORIGIN, INCLUDING ACQUIRED IMMUNE DEFICIENCY SYNDROME

CROSS-REFERENCE TO RELATED APPLICATIONS

The present invention is a continuation-in-part of co-pending U.S. patent application Ser. No. 692,822, filed Jan. 18, 1985, now U.S. Pat. No. 4,692,332, issued Sept. 8, 1987.

BACKGROUND OF THE INVENTION

The present invention pertains in general to immunotherapeutic techniques for treating diseases of viral origin. In particular, the present invention pertains to immunotherapeutic techniques useful in treatment of disease states such as feline leukemia, bovine leukemia, acquired immune deficiency syndrome (AIDS), and acquired immune deficiency syndrome related complex (ARC).

In order to protect the integrity of the organism, higher vertebrates possess an elaborate immune system which distinguishes foreign substances, which must provoke an immune response in order to be eliminated, from "self" substances, which are tolerated. The mechanism that effectuates this discrimination between self and foreign substances is known to involve interactions among types of white blood cells (leukocytes).

Upon exposure to the circulating fluids of the body, substances capable of recognition by the immune system (antigens) come into contact with a type of leukocyte called a macrophage. Macrophages are phagocytic cells and can therefore engulf and destroy those materials which are not protected from them by size, surface texture (i.e., smoothness), surface charge, or some other mechanism.

Once engulfed and processed by a macrophage, an antigen or a portion thereof is presented at the surface of the macrophage for contact with another type of leukocyte called a thymocyte or T-cell. T-cells control the production of antibodies by yet another type of lymphocyte called a B-cell.

Antibodies are B-cell-produced proteins which are capable of combining with an antigen in a reaction which is specific for that antigen. An antibody only combines with certain portions (antigenic determinants) of the surface of the antigen, so that the antibody is specific to the degree that the determinant with which it combines is not also found on other antigens.

The binding of an antibody to its corresponding antigen on the surface of a foreign cell has significant consequences related to the destruction of that cell by the immune system. First, the coating of the cell by antibody facilitates ingestion of the cell by macrophages and by other types of phagocytes including killer (K) cells, which act to destroy antibody-coated cells but which do not require sensitization by prior exposure with macrophage-processed antigen, and polymorphonuclear (PMN) leukocytes. Second, the coating of a cell by antibody activates a system of proteins, known as the complement system, in the liquid (plasma) fraction of the blood. Upon activation of this system, complement components also coat the foreign cell, which facilitates phagocytosis. In addition, complement activation results in the stimulation of inflammatory cells, leading to production of chemicals which attract macrophages through a process called chemotaxis and leading to inflammatory hormone-like activation of cellular functions. Lastly, complement components act directly to break up (lyse) the membrane of the foreign cell. The portion of the immune response involved with antigen-antibody and complement interactions is generally referred to as the humoral reaction.

T-cells, which regulate the humoral reaction, are of several types. These types of T-cells have been described as including helper ($T_H$) cells, inducer ($T_I$) cells, regulator ($T_R$) cells, and suppressor ($T_S$) cells. Herscowitz, Chapter 7 in *Immunology III*, Bellanti, J. W. Saunders, Philadelphia (1985). $T_I$ and $T_H$ cells are mobilized by contact with processed antigen on the surface of macrophages. $T_H$ cells are also activated by signals from $T_I$ and from $T_R$ cells. $T_R$ cells are activated by signals from $T_I$ and $T_S$ cells. Mobilization of $T_S$ cells occurs in response to signals from $T_R$ cells or as a result of contact with antigen.

Introduction of an optimal amount of a foreign substance into the fluids of the body initiates a process which results in production of antibody by B-cells. In this process, B-cells respond to stimulation by $T_H$ cells, which have in turn been stimulated by macrophages. Introduction of a persistent low level of some antigens or of a high level of an antigen results in a low-level of or in a lack of production of antibody due to an interruption by $T_S$ cells of the signals from $T_H$ cells to B-cells. This interruption, called suppression, may be induced through the macrophage-$T_I$-$T_R$ pathway or by direct stimulation of the $T_S$ cells by antigen. Suppression of antibody production to a first antigen may be overcome in a process known as contrasuppression through the stimulation of a subtype of $T_S$ cells called contrasuppressor cells by a second antigen which is antigenically similar to the first antigen. These contrasuppressor cells send a signal to $T_R$ cells which render the $T_H$ cells resistant to the activity of the suppressor $T_S$ cells and which interrupt the suppressor signals of the suppressor $T_S$ cells. See Gershon, et al., *J. Exp. Med.*, 153:1533–1546 (1981); Yamauchi, et al., *J. Exp. Med.*, 153:1547–1561 (1981); and Green, et al., *Ann. Rev. Immunol.*, 1:439–463 (1983).

It is the balance of the actions of $T_H$ helper and $T_S$ suppressor cells which determines whether an immune response develops in the presence of an antigen. Thus, as a practical matter, the functioning of the network of T-cells may be viewed in terms of the ratio of helper to suppressor cells ($T_H/T_S$).

T-cells are also involved in another type of immune response which is said to involve cell-mediated immune (CMI) reactions. Contact of $T_H$ cells with macrophage-processed antigen causes the $T_H$ cells to release interleukin II (IL-2), which activates cytotoxic ($T_{CYT}$) T-cells and, in conjunction with gamma interferon also released by the $T_H$ cells at this time, activates natural killer (NK) cells. Both $T_{CYT}$ and NK cells kill foreign cells. $T_{CYT}$ cells are particularly involved with rejection and with the destruction of tumor cells.

As is evident from the foregoing discussion, a general outline of the functioning of the immune system is available. However, many areas of the functioning of the immune system remain unclear. One of these areas relates to the apparent inability of the immune system to recognize certain cancers (malignant neoplasms) and cells infected with certain viruses, e.g., feline leukemia virus; bovine leukemia virus; and human T-leukemialymphoma virus (HTLV), which is believed to be the causative agent in AIDS.

In attempts to stimulate an immune response against a malignant neoplasm, many approaches have been aimed at the augmentation of antitumor defenses by administration of adjuvants (immune enhancers or potentiators). These approaches attempt to enhance nonspecific phagocytosis and killing of tumor cells by macrophages and T-cells. Such approaches employ infectious BCG mycobacteria, non-living *Corynebacterium parvum*, glucan (a glucose polymer derived from microorganisms), or levamisole (an antihelminthic drug known to be useful for stimulating CMI and the action of macrophages). Herberman, et al., Chapter 19 in *Immunology III* (Bellanti, ed.), W. B. Saunders Co. (1985), at page 343. The reported antitumor action of lysosome and pepsin lysates containing glycopeptides from the cell wall of *Lactobacillus bulgaricus* [Bogdanov, et al., *FEBS Letters*, 57:259 (1975); Bogdanov, et al., *Byulletin Eksperimental'noi Biologia i Meditsiiny*, 84:709 (1977)] and the treatment of malignant tumors with destroyed *Staphylococcus aureus* [abstract of examined Japanese Patent Application No. 84 046487] appear also to fall in this category. Adjuvant therapy has had varying degrees of questionable or limited success. Herberman, et al., supra.

The failure of the immune system to recognize malignant neoplasms is particularly puzzling in view of the fact that certain characteristic substances (tumor markers) are present at levels which are elevated above normal in patients with various neoplastic disease states. Specifically, alphafetoprotein (AFP), carcinoembryonic antigen (CEA), and human chorionic gonadotropin (HCG) are oncofetal tumor markers widely used in the investigation of patients with neoplasms of the liver, colon, and trophoblast, respectively. AFP has been found at levels elevated above normal in fifty percent or more of patients with yolk sac tumors, hepatomas, retinoblastomas, embryonal carcinomas, breast carcinomas, and carcinomas of the uterine cervix, and has been found at elevated levels in between two and fifty percent of patients having carcinomas of the pancreas, melanomas, gastric carcinomas, basal cell carcinomas, bronchogenic carcinomas, pancreatic carcinomas, medullary thyroid carcinomas, familial medullary thyroid carcinomas, osteosarcomas, retinoblastomas, ovarian cystadeno-carcinomas, mycosis fungoides, hepatomas, esophageal carcinomas, adenocarcinomas of the uterine cervix, lung carcinomas, carcinomas of the small intestine, urinary bladder carcinomas, and renal cell carcinomas, and has been found at elevated levels in between nine and fifty percent of patients having neural crest tumors, breast carcinomas, prostatic carcinomas, primary uveal carcinomas, neuroblastomas, fluids with malignancy, seminomas, basal cell carcinomas, gastric carcinomas, laryngeal carcinomas, endometrial carcinomas, uterine cervix intraepithelial carcinomas, carcinomas of the buccal mucosa, craniopharyngiomas, embryonal rhabdomyosarcomas, carcinomas of the oropharynx, brain tumors and testicular teratomas. HCG has been found at elevated levels in the serum of fifty percent or more of patients having choriocarcinomas, malignant interstitial cell tumors of the testis, non seminomatous tumors of the testes, embryonal carcinomas, and pancreatic carcinomas, and has been found at elevated levels in between six and fifty percent of the patients having teratomas, ovarian adenocarcinomas, uterine cervix carcinomas, endometrial carcinomas, seminomas, gastric carcinomas, urinary bladder carcinomas, breast carcinomas, colorectal carcinomas, bronchogenic squamous cell carcinomas, melanomas, and multiple myelomas. Other universal oncofetal tumor markers, including tissue polypeptide antigen (TPA), which is associated with cell proliferation and which is not specific for any species, are also known. See, Klavins, *Annals of Clinical and Laboratory Science*, 13:275–280 (1983).

With respect to HCG, a chorionic gonadotropin-like antigen has been found in bacteria isolated from the urine of cancer patients, as indicated in Acevedo, et al., *Infection and Immunity*, 31:487–494 (1981), but not in the same species of bacteria obtained from any other source tested. Furthermore, rat mammary adenocarcinoma cells and rat hepatoma cells have been found to synthesize chorionic gonadotropin-like material, although no such material was found in the sera of the animals bearing these neoplasms, in Kellen, et al., *Cancer Immunol. Immunother.*, 13:2–4 (1982). In the papers of Kelle, et al., and in U.S. Pat. No. 4,384,995, a subunit of HCG conjugated to tetanus toxoid is used to prophylactically stimulate an immune response to chorionic gonadotropin-like substances by repeated injection with the conjugated material before exposure to tumor cells known to bear a chorionic gonadotropin-like antigen.

Among the differences between prophylactic treatment with HCG and the adjuvant therapy approach is that the induction of an immune response for prophylactic purposes requires repeated injections over a period of time in order to initiate the development of at least one population of identical B-cells (a clone) producing a given antibody to a tumor antigen and for antibody to be produced by that clone. On the other hand, adjuvant therapy may result in antibody production by an existing clone of B-cells and thus has antitumor effects which may be immediately observed. Therapeutic treatment (i.e., treatment after a malignant neoplasm is present) with HCG conjugated with tetanus toxoid raises the possibility of an uncontrollable Herxheimer-type reaction. The Herxheimer reaction appears after treatment of syphilis patients with a substance that is toxic to the causative spirochete bacteria, which bacteria thereupon die in massive numbers, releasing potentially fatal toxic substances from the bacteria into the blood stream. By analogy, at some as yet unpredictable point in the induction of an immune response to a tumor antigen, a massive die-off of cancer cells may result in the death of the patient.

A luteinizing hormone releasing factor (LHRF), sometimes generically referred to as gonadorelin, which causes luteinizing hormone, a pituitary gonadotropin, to be released from the pituitary, has been used for treating various tumors in U.S. Pat. Nos. 4,002,738 and 4,071,622. Gonadorelin has also been used in the treatment of benign prostatic hyperplasia, a type of non-malignant but excess prostatic growth, in U.S. Pat. No. 4,321,260. However, no indication is provided in these patents that direct application of any gonadotropin may affect destruction of malignant neoplasms. In addition, release of LH from the pituitary is subject to a feedback control independent of the administered gonadotropin, so that how much, if any, LH released is not determinable merely from knowledge of an administered dose. Moreover, LHRF in combination with other substances may act to increase chorionic gonadotropin secretion by direct action on a tumor cell, further compounding the uncertain effect of LHRF administration. Kellen, et al., *AACR Abstracts,* 23:235 (March 1982) (Abstract 928).

In fact, Simon, et al., *J.M.C.I.,* 70:839–845 (1983), indicates that dosages of gonadotropic and steroid hormones stimulate the growth of differentiated carcinomas. These hormones include human follicle-stimulating hormone (FSH), HCG, human luteinizing hormone (LH), and cortisol. Thus Simon, et al., appears to support the idea that direct administration of gonadotropic or steroid hormones has a proliferative effect on malignant neoplasms.

Evidence for the suppression of the immune response against antigens of neoplastic cells is provided by Akiyama, et al., *J. Immunol.,* 131:3085–3090 (1983), wherein responsiveness of a mixed culture of lymphocytes from cancer patients and healthy donors was suppressed by the introduction into the system of tumor cells from the cancer patients. This suggests that among the lymphocytes of the cancer patients were $T_S$ cells specific for tumor-derived cells, inasmuch as the response of cultures containing only lymphocytes from healthy donors was not so suppressed.

Furthermore, antigen-specific $T_S$ cells have been isolated from a mouse having a plasmacytoma, which cells inhibited the in vitro induction of a cytotoxic T-cell response against the tumor. Kolsch, *Scand. J. Immunol.,* 19:387–393 (1984). According to Kolsch, $T_S$ cells may be activated and may dominate $T_H$ cells by high and low doses of antigen, but a critical, intermediate antigen dose which activates $T_H$ cells at the same time as it activates the $T_S$ cells, permits $T_H$ cells to dominate. Thus, Kolsch indicates that there may be an antigen dose at which a delicate balance is reached where $T_H$ cells are activated but at which $T_S$ cells dominate the immune response.

In Loblay, et al., *Aust. J. Exp. Biol. Med. Sci.,* 62:11–25 (1984), it is indicated that the suppression produced by $T_S$ cells in animals which have been exposed to an antigen is enhanced by a subsequent administration of a sufficiently large dose of antigen. Perhaps it is not so surprising, therefore, that attempts to induce contrasuppression have been aimed at supplying contrasuppressor cells, or substances therefrom, rather than by direct induction of contrasuppression. See, Green, "Contrasuppression: Its Role in Immunoregulation", in *The Potential Role of T-Cells In Cancer Therapy,* Fefer, et al., eds., Raven Press, New York (1982); and Green, et al., *Ann. Rev. Immunol.,* 1:439–463 (1983).

The methods and compositions disclosed in this application utilize unusually low levels of ingredients which yield surprising and unexpected results given the low levels actually employed. Applicants note however that a recent study, Reily, D. T., et al., *Lancet, II,* 881–886 (1986) tested whether homeopathic potencies are merely placebos in a randomized, double-blind, placebo-controlled trial. Homeopathy involves administering a greatly attenuated preparation of an agent which closely mimics the patients symptoms. The results indicated that homeopathically treated patients showed a significant reduction in patient and doctor assessed symptoms associated with active hay fever. Thus, no evidence emerged to support the idea that placebo action fully explains the positive clinical responses to homeopathic drugs. The article does not disclose or suggest a treatment for AIDS.

U.S. Pat. No. 4,410,510, issued to Livingston-Wheeler on October 1983, uses choriogonadotropin-like material (see column 6, lines 34–7), i.e., material that cross-reacts with anti-HCG antibodies in a pregnancy test kit and RIA, to treat chickens for a virally-induced tumor. However, Livingston-Wheeler does not disclose the use of ECG (equine chorio gonadotropin) or HCG, the use of a lysate of *S. aureus* as an immune enhancer, or that either or a combination of both should be used in a dose lower than that required to provoke a humoral immune response.

Knecht, *Chem. Abstracts,* 92:88377m (1980); provides negative results for the use of a HCG beta-subunit coupled to tetanus toxin in a study in which hamsters implanted with a human carcinoma were treated. Thus, Knecht does not disclose the use of ECG, the use of a lysate of *S. aureus* as an immune enhancer, or that either ECG or HCG or a combination of either with a bacterial lysate should be used in a dose lower than that required to provoke a humoral immune response.

Melmed, *Chem. Abstracts,* 99:689a (1983); reports that HCG stimulates proliferation of Nb2 rat lymphoma cells in vitro, with no effect being observed for subunits of HCG. Thus, Melmed does not disclose the use of ECG or HCG in the treatment of AIDS, the use of a lysate of *S. aureus* as an immune enhancer, or that either or a combination of both should be used in a dose lower than that required to provoke a humoral immune response.

Papademeteriou, *Chem. Abstracts,* 96:15389 (1982); reports that injection of 500 IU of HCG for six days in vivo or exposure of isolated macrophages to >100 IU/ml in vitro rendered peritoneal macrophages cytotoxic against MLB-2 leukemia cells. However, Papademeteriou does not disclose the use of ECG in the treatment of AIDS, the use of a lysate of *S. aureus* as an immune enhancer, or that either or a combination of both should be used in a dose lower than that required to provoke a humoral immune response.

Crockford and Burchiel U.S. Pat. No. 4,323,546, as reported in Crockford, April 1982, *Chem. Abstracts,* 92:176610n (1980); U.S. Pat. No. 4,311,688, Burchiel, January 1982 as reported in *Chem. Abstracts,* 95:86351m (1981), discloses only the use of anti-HCG antibodies and not HCG in the detection of cancers. Neither Crockford nor Burchiel discloses the direct administration of ECG or HCG in the treatment of AIDS, the use of a lysate of *S. aureus* as an immune enhancer, or that either or a combination of both should be used in a dose lower than that required to provoke a humoral immune response.

Fuji Zoki Seiyaku (Derwent Abstract No. 89190 of a Japanese application published 10/31/80) discloses the use of an immunopotentiator produced by destroying *S. aureus* cells in the treatment of malignant tumors. However, Fuji Zoki Seiyaku does not disclose the use of ECG or HCG in the treatment of AIDS, or that a bacterial lysate or a combination of a lysate and HCG or ECG should be used in a dose lower than that required to provoke a humoral immune response.

Hlavayova, *Chem. Abstracts,* 100:96263v (1984), discloses that staphylotoxin-treated sarcoma cells exhibit decreased growth rates when transplanted into susceptible hosts. However, Hlavayova does not disclose the use of ECG or HCG in the treatment of AIDS, or that either a bacterial lysate or a combination of a bacterial lysate and a chorionic gonadotropin should be used in a dose lower than that required to provoke a humoral immune response.

Cooper, *Chem. Abstracts,* 100:84075x (1984), discloses that serum treated with fixed *S. aureus* and injected intraperitoneally into tumor-bearing mice increased mean survival time. However, Cooper does not disclose the use of ECG or HCG in the treatment of AIDS, the use of a lysate of S. aureus as an immune enhancer, or that either or a combination of both should be used in a dose lower than that required to provoke a humoral immune response.

Liu, Chem. Abstracts, 101:70689j (1984), discloses that ex vivo immunoabsorption with Staphylococcus protein A-based filters results in a response to therapy in most feline leukemia virus-infected cats tested. However, Liu does not disclose the use of ECG or HCG in the treatment of AIDS, the use of a lysate of S. aureus as an immune enhancer, or that either or a combination of both should be used in a dose lower than that required to provoke a humoral immune response.

Liu, Chem. Abstracts, 101:228353q (1984), discloses injection of purified S. aureus protein A into cats infected with feline leukemia virus leading to a loss in viremia and to a correction of cytological and hematological abnormalities. However, Liu does not disclose the use of ECG or HCG in the treatment of AIDS, or that either a bacterial lysate or a combination of a bacterial lysate and a chorionic gonadotropin should be used in a dose lower than that required to provoke a humoral immune response.

Cohen, Chem. Abstracts, 101:65664t (1984), discloses the treatment of venereal tumor-bearing dogs and guinea pigs with Staphylococcus aureus protein A injection and reports no regression of the tumors. Thus Cohen does not disclose the use of ECG or HCG in the treatment of AIDS, the successful use of a lysate of S. aureus as an immune enchancer, or that either or a combination of both should be used in a dose lower than that required to provoke a humoral immune response.

Langcone, Chem. Abstracts, 101:88606 (1984), discloses that intact S. aureus cell wall and even relatively high does of Sepharose TM are active in generating complement. However, Langcone does not disclose the use of ECG or HCG in the treatment of AIDS, the use of a lysate of S. aureus as an immune enchancer, or that either or a combination of both should be used in a dose lower than that required to provoke a humoral immune response.

Balint, Chem. Abstracts, 100:839365 (1984), discloses that perfusion of sera from normal and breast adenocarcinoma-bearing humans or dogs through immobilized staphylococcal protein A produces eluates which are tumoricidal and toxic upon reinfusion into the subject. However, Balint does not disclose the use of ECG or HCG in the treatment of AIDS, or that a bacterial lysate or a combination of a bacterial lysate and a chorionic gonadotropin should be used in a dose lower than that required to provoke a humoral immune response.

Chugai, Chem. Abstracts, 101:235588r (1984), discloses an anti-leukemic activity in mice of an isolate of S. aureus. However, Chugai does not disclose the use of ECG or HCG in the treatment of AIDS, or that either a bacterial lysate or a combination of a bacterial lysate and a chorionic gonadotropin should be used in a dose lower than that required to provoke a humoral immune response.

Mitsui, Chem. Abstracts, 101:17331k (1984), discloses that heat denatured DNA isolated from S. aureus inhibits neoplasms. However, Mitsui does not disclose the use of ECG or HCG in the treatment of AIDS, or that a bacterial lysate or a combination of a bacterial lysate and a chorionic gonadotropin should be used in a dose lower than that required to provoke a humoral immune response.

Miyakoshi, Chem. Abstract, 96:671278, (1982), reports Staphage lysate to be a useful mitogen for the in vitro study of cell-mediated immunity. However, Miyakoshi does not disclose the use of ECG or HCG in the treatment of AIDS, the use of a lysate of S. aureus as an immune enchancer, or that either or a combination of both should be used in a dose lower than that required to provoke a humoral immune response.

SUMMARY OF THE INVENTION

A method according to the present invention for alleviating symptoms of acquired immune deficiency syndrome in a disease victim comprises the steps of administering to the disease victim a member selected from the group consisting of characteristic substances of diseased cells of the acquired immune deficiency syndrome victim and effective fragments and effective derivatives thereof, in a pharmaceutically effective amount which is less than the lowest amount necessary to provoke a humoral immune response, as exemplified by the determination of a positive wheal upon subcutaneous injection. Illustrative of such a method is the administration of a composition including human chorionic gonadotropin (HCG), a lysate of S. aureus, influenza virus vaccine, and fractionated inactivated HIV virus.

A composition according to the present invention for alleviating symptoms of acquired immune deficiency syndrome in a disease victim comprises a member selected from the group consisting of characteristic substances of diseased cells of the acquired immune deficiency syndrome victim and effective fragments and effective derivatives thereof, in a pharmaceutically effective amount which is less than the lowest amount of the substance necessary to induce a humoral immune response. This composition also comprises an immune enhancer, such as BCG mycobacteria, Corynebacterium parvum, and levamizole, in an amount less than the lowest amount of the substance necessary to provoke a humoral immune response, as exemplified by the determination of a positive wheal upon subcutaneous injection. Illustrative of such a composition are compositions including HCG, a lysate of S. aureus, such as Staphage Lysate TM, an influenza virus vaccine, such as Fluogen TM, and fractionated inactivated HIV virus. This composition is referred to below as Solution I. Solution II is similar to Solution I and contains the same components with the exception that fractionated inactivated HTLV-III virus is omitted and replaced with peptide T of HIV.

DESCRIPTION OF THE PREFERRED EMBODIMENT

In a method according to the present invention, a substance characteristic of AIDS is administered to a patient afflicted with AIDS in an amount which is believed to be less than the lowest amount necessary to provoke a humoral immune response (that is, to begin production of antibody). This dosage is administered daily until disappearance of the symptoms of the disease, and may be administered longer without harm if so desired. The symptoms alleviated include fever, night sweats, malaise/fatigue, enlarged nodes, weight loss, diarrhea and opportunistic infections.

In order to identify a dose lower than that required to provoke a humoral immune response, a wheal produced upon subcutaneous injection of the therapeutic material is evaluated according to the procedure set forth in Moore, *Clinical Medicine,* 81:16-19 (1974), wherein such evaluation is employed to identify a dosage of vaccine useful in the eradication of the symptoms of influenza. Upon subcutaneous injection, a wheal may be determined to be positive ten minutes after injection as blanched, hard, raised and discoid (regular, sharply demarcated edges, as though a disc has been cemented to the skin). A negative wheal, indicative of a dose below that necessary to provoke an immune response, is so absorbed at the end of ten minutes that it is softer and flatter than at injection, may have an irregular or ragged edge, and has grown less than an average of two millimeters in diameter from its original size.

Although a preferred dosage of 2 International Units (IU) was initially determined by skin tests of the horse of Example 1, the Examples below indicate that successful therapy may often be achieved by administering a dose at an initial level of 2 IU without an initial dosage level determination. A dose of 2 IU appeared to be low enough for any animal or human tested, even without first determining optimum dose by a skin test. However, it is believed that determination of a proper dosage, as exemplified above or otherwise, may be used by those skilled in the art to refine the method according to the present invention.

To complement the activity of the chorionic gonadotropin, and to simultaneously guard against a toxic reaction induced by a rapid sloughing of necrotic tissue analogous to a Herxheimer-type reaction, a bacterial lysate was added to each treatment vial as a broad-spectrum stimulator of cell-mediated immunity, i.e., as an immune enhancer. No species specificity of response was observed, to the extent that a human cancer patient has responded to either of equine chorionic gonadotropin (ECG) or HCG, and that other animals of the examples have also responded favorably to treatment with either ECG or HCG.

AIDS patients have been reported as exhibiting a marked reduction in the ratio of $T_H$ to $T_S$ cells. See, Cohen, *British Journal of Hospital Medicine,* 31:250-259 (1984). It has been reported that the virus thought to cause AIDS is a type of human T-cell leukemia-lymphoma virus (HTLV) known as HTLV-III virus and that this virus is related to the virus which causes feline and bovine leukemia. Franklin, *Science News,* 126:269 (1984). Feline and bovine leukemia viruses are known to be antigenically similar. Morgan, et al., *J. Virol.,* 46:177-186 (1983). Accordingly, the discovery by the present inventor that a dose of HCG which is lower than that required to provoke a humoral immune response may be effective in the alleviation of the symptoms of feline leukemia and of bovine leukemia, indicates the potential effectiveness of an analogous form of treatment in the alleviation of the symptoms of AIDS as well.

Furthermore, feline leukemia virus (FLV) and HTLV are both retroviruses (also known as Type C viruses, RNA tumor viruses, or leukemia viruses). Manzani, et al., *Surv. Immunol. Res.,* 1:122-125 (1982). A retrovirus may be transmitted as an infectious particle containing viral genes encoded in the form of ribonucleic acid (RNA). Within an infected cell this RNA is encoded into deoxyribonucleic acid (DNA) by a viral enzyme called reverse transcriptase. The DNA-encoded viral genes are thereafter integrated with and replicated, transcribed and translated along with the DNA-encoded genetic material of the infected cell. Lewin, Chapter 13 in *Genes,* John Wiley and Sons, New York (1983). Such retroviruses generally produce steady state infections where viral progeny are continually extruded by budding from the surfaces of host cells. Thus, steady state viruses exhibit the clinical criteria for the induction of tolerance in that there is a high dose inoculum of viral antigen, the virus-specific antigen persists, and tumor-specific antigens are developed and persist. See Herberman, et al., supra.

Methods and compositions according to the present invention are shown in the examples below to be effective in the treatment of feline and bovine leukemia among other neoplastic diseases. Similar methods and compositions according to the present invention are effective in the treatment of AIDS.

Examples 1, 2 and 3 below relate to the treatment of horses afflicted with two different types of malignant neoplasms.

Examples 4 and 5 below relate to the treatment of cats diagnosed as having feline leukemia.

Example 6 below relates to the treatment of cows afflicted with bovine leukemia.

Examples 7 and 8 below relate to the treatment of dogs afflicted with two different types of malignant neoplasm.

Example 9 below relates to the treatment of human patients afflicted with malignant neoplasms.

Example 10 below relates to the treatment of human patients diagnosed as having AIDS or ARC (AIDS Related Complex).

EXAMPLE 1

A horse with mastocytoma was treated with 2 IU per day of gonadotropin only (i.e., without the bacterial lysate immune enhancer). The gonadotropin used was equine chorionic gonadotropin, supplied by the W. A. Butler Company, or human chorionic gonadotropin, supplied by the Ayerst Corp. (as A.P.L.—human chorionic gonadotropin). In this example and in the examples which follow, a dosage of 2 IU per day of either equine chorionic gonadotropin (ECG) or HCG was used.

The horse showed rapid and significant diminution of tumors before succumbing to an Herxheimer-type reaction. (No such adverse effect was seen in other treated animals when an immune enhancer was coadministered).

EXAMPLE 2

Three horses with melanoma were successfully treated, to the point of the disappearance of symptoms, according to the procedure of Example 1 above, but with the addition of a bacterial lysate immune enhancer. After the symptoms disappeared, the three animals received no further treatment and exhibited no recurrence of symptoms.

A suitable bacterial lysate immune enhancer, such as *S. aureus,* for employment in this procedure is sold under the name Staphage Lysate ™, available from Delmont Labs. Staphage Lysate ™ is a bacteriologically-sterile staphylococcal vaccine containing components of *Staphylococcus aureus* and culture medium ingredients (sodium chloride and ultrafiltered beef heart infusion broth). The staphylococcal components are prepared by lysing parent cultures of *S. aureus,* serologic types II and III, with a polyvalent staphylococcus bacteriophage. Each milliliter contains 120–180 million colony-forming units (cfu) of *S. aureus* and 100–1000 million staphylococcus bacteriophage plaque-forming units (pfu).

All treatment trials contained 2 IU gonadotropin plus 0.1 cc Staphage Lysate ™ in each 0.5 cc shot. Regardless of species, type of malignancy, or size of cancer, all animals received a once-daily subcutaneous injection of the admixture of chorionic gonadotropin and immune enhancer until the tumor or leukemia had disappeared. All animals were diagnosed as having cancer by a licensed veterinarian.

EXAMPLE 3

One horse with an undifferentiated carcinoma of the face was successfully treated according to the procedure of Example 2 to the point of the disappearance of symptoms. After disappearance of the symptoms, the horse received no further treatment and exhibited no recurrence of symptoms.

EXAMPLE 4

A double-blind test of treatment of cats diagnosed as being infected with feline leukemia virus was conducted by a licensed testing laboratory. Laboratory tests for feline leukemia were conducted by a licensed laboratory, and biopsy tissue from some cases was examined by a veterinary reference laboratory. In all cases animals were treated as above, with termination of treatment coinciding with disappearance of symptoms. In no cases was it necessary to resume therapy for a second round of treatment. No side effects have been observed.

A double blind evaluation of the efficacy of daily doses of the combination of gonadotropin (2 units per dose) and Staphage Lysate ™ (0.1 cc per dose) in cats with advanced leukemia was conducted under the supervision of, and the personnel for, TechAmerica, Inc. at their facility in Fort Collins, Colo. Eight cats received treatment with the test material, while four received placebo (phenolated saline) daily injections. The results are indicated in Table 1 below.

TABLE 1
RESULTS OF ADMINISTRATION OF HCG & SPL
TO CATS WITH ADVANCED FELINE LEUKEMIA

| ANIMALS RECEIVING ADMIXTURE | | | |
|---|---|---|---|
| Cat Number | Survival (days) | Viremia | Tumor Mass |
| 2 | 16 | Decreased | No change |
| 3 | 42 | Ceased | Reduced to Normal |
| 7 | 4 | No Test | No Test |
| 11 | 19 | Slight Decrease | No change |
| 15 | 10 | No Change | Slight Decrease |
| 21 | 51 | No Change | Reduced to Normal |
| 23 | 51 | Decreased | Reduced to Normal |
| 24 | Euthanized at 40 | No Change | Reduced to Normal |
| ANIMALS RECEIVING PLACEBO | | | |
| Cat Number | Survival (days) | Viremia | Tumor Mass |
| 4 | 1 | No Test | No Test |
| 5 | Euthanized at 10 | No Change | No Change |
| 16 | 6 | No Test | No Change |
| 22 | 6 | No Test | No Test |

All animals receiving a placebo died within 7 days. Some treated animals were still alive after six weeks, and were receiving no further treatment. Of special interest was the observation that several treated cats were not only asymptomatic, but also non-viremic. In any event, survival was prolonged and/or symptoms were alleviated for 6 (cats numbered 2, 3, 11, 21, 23 and 24) of 8 treated animals, as compared to the animals receiving a placebo (cats numbered 4, 5 16 and 22 received a placebo).

Cat number 4 died one day after the start of the test. Cat number 4 was not necropsied. Cat number 5 showed no significant change in viremia. Tumor size remained constant. The cat was euthanized on day 10 of the test. At necropsy, the cat was observed to be moribund, thin, blind and anemic. Tumors were located on the tongue, and eyes, and in the pleural, perirenal and peritoneal cavities. Cat number 16 died six days after initial treatment. Upon necropsy, small metastatic tumors were observed in the lungs, and large tumors were observed in the omentum. Cat number 22 died six days after initial treatment. Upon necropsy, metastatic tumors were found in the lung, in the liver and in the omentum. The cause of death was renal hemorrhage into the retroperitoneal sublumbar region.

Cats numbered 2, 3, 7, 11, 15, 21, 23 and 24 received the experimental treatment.

In cat number 2, viremia decreased but the tumor remained the same size. Cat number 2 died 16 days after the start of the test. At necropsy, a tumor was found which was open and which had drained. General lymph node enlargement, an enlarged liver, and a small tumor in the apex of the heart were also noted.

In cat number 3, viremia decreased to negative. The tumor decreased in size back to a normal condition. The cat was normal in appearance during the test.

Cat number 7 died four days after initial treatment. No necropsy was performed.

Cat number 11 exhibited a slight decrease in viremia. Tumor size remained the same. Cat number 11 died 19 days after initial treatment. Upon necropsy, tumors were found throughout the body cavity.

Cat number 15 showed no significant decrease in viremia. No change in the tumor was observed. The cat died 10 days after initial treatment. At necropsy, the cat was observed to be emaciated, and tumors were found in the lungs, mediastinum, pericardia, pleura and illiac lymph nodes.

In cat number 21 the viremia was constant. The cat appeared normal. Upon necropsy, an enlarged thymus and enlarged mesenteric lymph nodes were observed.

In cat number 23, viremia decreased through the course of the test. Cat number 23 remained normal throughout the duration of the test.

In cat number 24, viremia remained constant. The cat appeared normal throughout the duration of the test. Upon necropsy, an enlarged thymus was observed, but the cat was otherwise normal.

EXAMPLE 5

Several dozen cats have been successfully treated for feline leukemia according to the procedure of Example 2 above by veterinarians in Ohio, Pennsylvania and North Carolina. Based upon the reported observations of the veterinarians, at least 80% of the treated cats have returned to normal health after termination of therapy. For example, one cat exhibited little strength and its body weight was reduced from 13 pounds to 6 pounds. After ten days of therapy, the cat was mobile and active, and its weight had increased to ten pounds.

EXAMPLE 6

Twenty cases of bovine leukemia were treated according to the procedure of Example 2 above, with complete remission of symptoms for as long as 13 months. Milk production of 17 cows was both restored and enhanced. Only three failures occurred, and in each case the cow had been moribund for several days before initiation of therapy. Laboratory tests for bovine leukemia were conducted by a licensed laboratory, and biopsy tissue from some cases was examined by a veterinary reference laboratory.

EXAMPLE 7

A squamous cell carcinoma on the jaw of a six-month-old pup was treated according to the procedure of Example 2 above. In spite of a "poor prognosis" from the veterinary reference laboratory examining the biopsy tissue, the dog entirely healed, as evidenced by sequential X-ray records.

A squamous cell carcinoma on the shoulder of a 12-year-old dog was treated according to the procedure of Example 2 above. After two days the dog could walk for extended periods, ate well, and the tumor became warm to the touch. Noticeable tumor shrinkage was observed after five days. After two weeks, the tumor was nearly resolved.

EXAMPLE 8

An anal tumor growing daily and laterally displacing the tail of a 13-year-old dog was treated according to the procedure of Example 2 above. The photographic record showed daily decrease in tumor size beginning on day three. The tumor resolved. The dog later died for unknown reasons. No necropsy was performed.

EXAMPLE 9

A limited number of human patients have been treated for cancers diagnosed as terminal, including melanoma and cancers of the colon, breast, liver, pancreas and lung. The patients were treated according to the procedure of Example 2 above, except that some patients received 0.2 cc of immune enhancer per dose rather than 0.1 cc per dose.

Of 9 patients treated at one location within a period of almost three years, all lived longer than the expected survival time initially indicated by their treating physicians. Patients began treatment with an expected survival of one month or less. As of August 1987, five of the nine patients had died. Two of the patients who died had discontinued treatment according to the present invention two months before death. Of the original nine patients, four survived more than 18 months, and, six survived 12 months since beginning treatment.

All nine patients practiced the method according to the present invention as a last resort, and all but the five patients who died, had had some form of radiation or chemotherapy prior to beginning therapy according to the present invention. All nine patients had diagnosed metastases indicative of an advanced disease state. No side effects were observed.

It is not clear, however, how regularly all patients administered the composition according to the present invention. For example, some surviving patients have decreased treatment to once or twice per week without a reduction in overall well-being. Of the four patients still surviving, one has entirely discontinued treatment with no sign of desease; two have continued treatment and have been disease-free for six months; and one has continued treatment and has a residual enlarged lymphoma node.

Sporadic treatment at other locations was not as successful, so that overall, about half of the treated patients are still surviving, while the other half have died. Due to the lack of autopsy data, it is not clear whether all of the deaths of treated patients may properly be attributed to cancer or to other causes.

Patients who had not received maximum chemotherapy and radiation responded most positively to the composition and method of the present invention. This suggests that the therapeutic agent of the present invention involves, at least in part, immune manipulation, and that the cells comprising the immune response are compromised in patients receiving traditional anti-cancer therapy.

EXAMPLE 10

Due to the complexity of the pathogenesis of AIDS and ARC (AIDS Related Complex), it is postulated that it is useful for a therapeutic agent to simultaneously (i) inhibit replication of the putative caustive agent (HIV); (ii) restore immune function in a controlled fashion to heal the compromised immune system without inducing auto-immunity or some other hyperimmune dysfunction; (iii) inhibit secondary viral infections such as those caused by the cytomegalovirus or Epstein Barr virus; and (iv) decrease the likelihood of complications from malignancies such as lymphomas or Kaposi's sarcomas which commonly further compromise the condition of the AIDS patient.

An admixture of substances was prepared with the following components. Chorionic gonadotropin was shown in the above examples, when used in low concentrations, to be extremely promising in treating a variety of malignant states in man and animals. It may be the case that chorionic gonadotropin alters the electrical charge on transformed cells thereby decreasing their relative negativity and thus rendering them more vulnerable to phagocytic and immune action. A bacterial lysate immune enhancer such as *S. aureus*, i.e., Staphage TM Lysate, was used in conjunction with chorionic gonadoptropin to enhance immune activity and to prevent the Herxheimer-type reactions that have been observed in animals treated with HCG alone. An influenza virus vaccine, such as Fluogen TM, when used in doses as low as one five hundredth the normal vaccine dose, is effective in controlling a variety of Herpes infections. An influenza vaccine, appears to be active at a level of immune responsiveness considerably different from that stimulated by vaccination, Miller, J. B., et al., *J. of Med. Assoc. of Alabama,* 41:493 (1972) and Miller, J. B., *Anals. of Allergy,* 42:295 (1979), and it was surmised that a low level of the AIDS agent, or its components, might perform the same way for the AIDS patient, i.e., stimulate the interference of virus infection and/or replication even in an immunologically compromised host. Accordingly, HIV virus fractions are also a component of the admixture.

An aqueous solution according to the present invention, (hereinafter solution I) for subcutaneous injection, containing the following combined components was prepared:

1. Human Chorionic Gonadtropin (APL) (Ayerst Labs, Division Home Products Corp., 685 Third Avenue, New York, N.Y.) diluted in phenolated saline such that each 0.5 cc dose contains 2.0 International Units.
2. Staphage Phage Lysate (SPL) (Delmont Laboratories, Inc., P.O. Box AA, Swathmore, Pa.), formulated to contain 120–180 million colony-forming units of *S. aureus* and 100–1000 million Staphylococcus bacteriophage plaque-forming units (Seriological Types I and III, with a polyvalent staphylococcus bacteriophage)—Each 0.5 cc dose contains 0.2 cc of this product.
3. 1:25 dilution of an influenza virus vaccine such as Fluogen ™ (Parke-Davis a Division of Warner-Lambert Co., 201 Tabor Road, Morris Plains, N.J.) influenza virus vaccine, formulated to contain no less than 45 μg of hemagglutinin antigen per 0.5 mL dose—Each 0.5 cc dose contains 0.05 cc of this dilution.
4. Fractionated inactivated HTLV-III virus (Organon Teknika Corp., 800 Capitol Drive, Durham, N.C.)—Diluted such that each 0.5 cc dose contains the equivalent of approximately four virus particles.
5. Phenolated Saline (Allergy Laboratories, Inc., 1005 SW Second Street, Oklahoma City, Okla.)—Normal saline with 0.4% phenol, used as supplied to bring up to a 0.5 cc dose.

Because Solution I consists of a combination of commercially available products, the preparation of the admixture to be evaluated consists solely of diluting the respective components to their appropriate concentrations and combining these dilutions into a final dosage for evaluation. Phenolated saline is used as a diluent throughout. The various components (except for the HTLV-III fraction) had been used safely alone or in various combinations for diseases other than AIDS. Further animal testing of one combination of two of the components of Solution I had proven significantly promising for the successful treatment of malignancies in animals as indicated in the above examples.

A pilot study of the use of the above aqueous solutions for the treatment of AIDS/ARC in five patients was conducted. Patients were treated with the Solution I admixture for 30 consecutive days, receiving 0.5 cc of the medicine subcutaneously each day. This period was followed by an equal period (30 days) without treatment, after which therapy was re-initiated and continued for an additional 13 months. The clinical results are summarized in Table 2 below. Table 3 lists the results of blood tests on these patients and Table 4 give the Natural Killer (NK) cell activity of these patients. Patients numbers 2, 4, and 5 received a modified version, referred to as Solution II, of the Solution I admixture one month prior to day 450, 409, and 444, respectively. This Solution II contained the same components as Solution I, listed on page 29, with the exception of component 4: the fractionated inactivated HTLV-III virus was omitted and replaced with "peptide T", an octapeptide (Ala-Ser-Thr-Thr-Thr-Asn-Tyr-Thr), corresponding to an amino acid sequence extant in HIV envelope glycoprotein gp 120, and which has been described in Pert, et al., *Proc. Nat'l. Acad. Sci.*, 83:9254-9258 (1986). Peptide T was purchased from Peninsula Laboratories, Inc.; 611 Taylor Way; Belmont, Calif. 94002. The total dose of Solution II administered daily was 0.5 cc and was diluted to a concentration of one $\times 10^{-16}$ mg per 0.5 cc dose.

TABLE 2

CLINICAL RESULTS OF ADMINISTRATION OF SOLUTION I

| Description | Patient Number | | | | |
|---|---|---|---|---|---|
| | 1 | 2 | 3 | 4 | 5 |
| Age | 40 | 30 | 34 | 30 | 28 |
| Race | C | C | C | C | C |
| Risk Group | HSex | HSex | HSex | BiSex | BiSex |
| Drug User | Nitrites | Nitrites | Nitrites | No | Varied |
| Clinical Group | ARC | ARC | ARC | ARC | ARC-AIDS |
| Symptoms (Initial) | | | | | |
| Fever | + | — | — | + | — |
| Night Sweats | — | — | — | + | + |
| Malaise/fatigue | + | — | + | + | + |
| Enlarged Nodes | + | + | + | + | + |
| Weight Loss | ± | — | — | ± | + |
| Diarrhea | + | — | — | — | ± |
| Opportunistic Infections | — | — | — | Candida HSV-1 | Bacterial Pneumonia |

Signs and Symptoms During First Ninety Days of Trial
(30 days on medication, 30 days off, 30 days on)

Patient #1 — Delayed hypersensitivity reaction at injection site; GI gas, sinusitis and diarrhea all more pronounced when off medication; sever tonsilitis when off medication.

Patient #2 — Some hypersensitivity at injection site; anxiety level increased during first course of therapy, then lessened; allergic sinusitis and rhinitis more pronounced off Solution I; fatigue increased off Solution I.

Patient #3 — Delayed reaction at injection sites; rapid resolution of HSV-II on Solution I; increased malaise and slower HSV-II resolution when off medication.

Patient #4 — Similar hypersensitivity pattern; calmer on medication; night sweats and node size and tenderness increased when off medication; leukoplakia when off medication.

Patient #5 — No hypersensitivity response on any injection; rapid decrease of night sweats and diarrhea with Solution I; feeling of "queasiness" when first on injections - followed injection by 10-15 minutes and lasted 1-2 hours; increased energy when on medication.

Clinical Status Approximately Ten Months After Initiation of Treatment

Patient #1 — Has gained weight, no opportunistic infections, good energy, no nodes.

Patient #2 — Continues well, has gained weight, no infections, no nodes.

Patient #3 — Continues well with respect to HSV-II, good energy, maintains weight after gaining slightly since start, nodes low.

Patient #4 — Former sense of nervousness and uneasiness has lessened markedly, weight steady, energy good, no night sweats.

Patient #5 — Continues to gain weight slowly, no nodes or sweats, no infections, good energy.

TABLE 3

Blood Parameters of Patients

| | | Patient #1 | | | | | |
|---|---|---|---|---|---|---|---|
| | Baseline | Treatment 7 Days | Treatment 28 Days | Off 30 Days | Treatment 14 Days | Treatment 28 Days | Treatment 365 Days |
| WBC | 7700 | 7500 | 6200 | 5900 | 5000 | 4700 | 4900 |
| Lymphs | 3400 | 3300 | 2300 | 2800 | 2400 | 2200 | 2100 |
| Segs | 48% | 45 | 55 | 44 | 45 | 50 | 41 |
| Bands | 1% | 3 | 2 | — | 3 | — | |
| Lymph | 44% | 44 | 37 | 47 | 48 | 46 | |

TABLE 3-continued
Blood Parameters of Patients

| | | | | | | | |
|---|---|---|---|---|---|---|---|
| Monos | 7% | 7 | 3 | 8 | 4 | 3 | |
| Eos | — | 1 | 3 | 1 | — | 1 | |
| $OKT_3$ | 79%/2685 | 75/2479 | 74/1702 | 75/2100 | 75/1800 | 79/1738 | 79/1559 |
| $OKT_{11}$ | 91%/3094 | 93/3069 | 91/2093 | 93/2604 | 90/2160 | 92/2024 | 89/1869 |
| $OKT_4$ | 15%/510 | 13/429 | 16/368 | 12/336 | 16/384 | 15/330 | 17/336 |
| $OKT_8$ | 63%/2142 | 60/1980 | 59/1357 | 61/1708 | 62/1488 | 63/1386 | 65/1365 |
| Ratio 4:8 | 0.2 | 0.2 | 0.27 | 0.2 | 0.26 | 0.2 | — |
| Leu16 | 2%/68 | 1/33 | 2/46 | 3/84 | 2/48 | 3/66 | 3/63 |

Patient #2

| | Baseline | Treatment 7 Days | Treatment 28 Days | Off 30 Days | Treatment 14 Days | Treatment 28 Days | Treatment 375 Days | Treatment 385 Days |
|---|---|---|---|---|---|---|---|---|
| WBC | 4700 | 4400 | 4100 | 3600 | 3200 | 3900 | 3500 | 4700 |
| Lymph | 2773 | 2400 | 1800 | 2300 | 1300 | 2300 | 2700 | 2800 |
| Segs | 27% | 41 | 50 | 33 | 48 | 32 | 21 | — |
| Bands | 2% | 2 | 2 | — | 5 | 1 | — | — |
| Lymphs | 59% | 54 | 43 | 64 | 42 | 59 | — | — |
| Monos | 9% | 3 | 1 | 3 | 3 | 8 | — | — |
| Eos | 3% | — | 4 | — | 2 | — | — | — |
| $OKT_3$ | 89.7%/2152 | 90/2160 | 90/1620 | 89/2047 | 92/1196 | 90/2070 | 87/2349 | 91/2548 |
| $OKT_{11}$ | 95.1%/2280 | 96/2304 | 87/1566 | 84/1932 | 94/1222 | 85/1955 | 83/2241 | 92/2576 |
| $OKT_4$ | 15.7%/377 | 15/360 | 16/288 | 16/368 | 16/208 | 15/345 | 11/297 | 10/280 |
| $OKT_8$ | 65.7%/1577 | 68/1632 | 68/1224 | 65/1495 | 64/832 | 64/1472 | 63/1700 | 71/1988 |
| Ratio 4:8 | 0.24 | 0.22 | 0.24 | 0.25 | 0.3 | 0.2 | — | — |
| Leu16 | 3.7% | 2/48 | 3/54 | 2/46 | 3/39 | 24/552 | 5/135 | 4.4/123 |

Patient #3

| | Baseline | Treatment 7 Days | Treatment 28 Days | Off 30 Days | Treatment 14 Days | Treatment 28 Days | Treatment 348 Days |
|---|---|---|---|---|---|---|---|
| WBC | 5200 | 5200 | 5500 | 4900 | 4400 | 4600 | 6300 |
| Lymph | 1400 | 1456 | 1900 | 2400 | 1000 | 1200 | 2300 |
| Segs | 61% | 58 | 48 | 44 | 66 | 66 | 36 |
| Bands | 4% | — | 6 | 1 | 1 | 1 | — |
| Lymph | 24% | 28 | 34 | 48 | 22 | 25 | — |
| Monos | 8% | 13 | 7 | 6 | 7 | 4 | — |
| Eos | — | 1% | 5 | 1 | 4 | 4 | — |
| $OKT_3$ | 82%/1148 | 85/— | 81/1539 | 77/1848 | 84/840 | 79/948 | 80/1840 |
| $OKT_{11}$ | 86%/1204 | 86.5/— | 88/1672 | 80/1920 | 90/900 | 84/1008 | 80/1840 |
| $OKT_4$ | 33%/462 | 26.2/— | 32/608 | 35/840 | 34/340 | 33/396 | 30/690 |
| $OKT_8$ | 44%/616 | 43/— | 53/1007 | 45/1080 | 49/490 | 44/528 | 49/1127 |
| Ratio 4:8 | 0.8 | 0.61 | 0.8 | 0.7 | 0.8 | 0.7 | — |
| Leu16 | 8%/112 | 8/— | 6/114 | 5/120 | 6/60 | 4/48 | 10/230 |

Patient #4

| | Baseline | Treatment 7 Days | Treatment 28 Days | Off 30 Days | Treatment 14 Days | Treatment* 28 Days | Treatment 334 Days | Treatment 344 Days |
|---|---|---|---|---|---|---|---|---|
| WBC | — | 6200 | 6200 | 6000 | 5700 | — | 4000 | 3900 |
| Lymph | — | 1300 | 1800 | 1700 | 2000 | — | 1100 | 1200 |
| Segs | — | 67% | 62 | 60 | 55 | — | 28 | — |
| Bands | — | 3% | 1 | 1 | 1 | — | — | — |
| Lymph | — | 21% | 29 | 29 | 35 | — | — | — |
| Mono | — | 8% | 4 | 9 | 5 | — | — | — |
| Eos | — | — | 4% | 1 | 3 | — | — | — |
| $OKT_3$ | 88% | 84/1092 | 84/1512 | 89/1513 | 87/1740 | — | 82/918 | 81/972 |
| $OKT_{11}$ | 91% | 82/1066 | 80/1440 | 92/1564 | 86/1720 | — | 83/930 | 87/1044 |
| $OKT_4$ | 26% | 26/338 | 23/414 | 22/374 | 23/460 | — | 19/213 | 18/216 |
| $OKT_8$ | 61% | 51/663 | 56/1008 | 57/969 | 56/1120 | — | 60/672 | 60/720 |
| Ratio 4:8 | 0.4 | 0.5 | 0.4 | 0.4 | 0.4 | — | — | — |
| Leu16 | 5% | 5/65 | 3/54 | 4/68 | 2/40 | — | 6/67 | 5.2/62 |

Patient #5

| | Baseline | Treatment 7 Days | Treatment 28 Days | Off 30 Days |
|---|---|---|---|---|
| WBC | — | 3300 | 3300 | 3700 |
| Lymph | — | 2000 | 1400 | 1600 |
| Segs | — | 28% | 30 | 46 |
| Bands | — | — | 4% | — |
| Monos | — | 8% | 21 | 11 |
| Eos | — | 3% | 2 | — |
| $OKT_3$ | 83% | 84/1680 | 80/1120 | 83/1328 |
| $OKT_{11}$ | 67% | 69/1380 | 61/854 | 72/1152 |
| $OKT_4$ | 21% | 25/500 | 24/336 | 20/320 |
| $OKT_8$ | 61% | 54/1050 | 57/798 | 62/992 |
| Ratio 4:8 | 0.3 | 0.2 | 0.4 | 0.3 |
| Leu16 | 4% | 2/40 | 5/70 | 5/80 |

*Data not determined.

TABLE 4
NATURAL KILLER CELL ACTIVITY OF PATIENTS UNDER TREATMENT

| PATIENT | DAYS ELAPSED | NK ACTIVITY 50/1 | NK ACTIVITY 25/1 |
|---|---|---|---|
| (1) | 0 | 21% | 8% |
|  | 10 | 54% | 34% |
|  | 21 | 31% | 21% |
|  | 38 | 22% | 13% |
|  | 65 | 28% | 13% |
|  | 94 | 19% | 8.7% |
|  | 170 | 70% | — |
|  | 430 | 6.4% | 1.6% |
| (2) | 0 | 19% | 12% |
|  | 10 | 14% | 9% |
|  | 31 | 5.4% | 2.2% |
|  | 59 | 24% | 9.4% |
|  | 73 | 4.2% | 1.9% |
|  | 85 | 8.3% | 5.8% |
|  | 113 | 32% | 18% |
|  | 146 | 22% | 16% |
|  | 409 | 6.6% | 0.0% |
|  | 440 | 6.8% | 1.5% |
|  | *450 | 93.0% | 15% |
| (3) | 0 | 17% | — |
|  | 4 | 26% | 12% |
|  | 26 | 16% | — |
|  | 63 | 42% | 24% |
|  | 77 | 8.9% | 3.4% |
|  | 89 | 31.7% | 12.8% |
|  | 117 | 35% | 21% |
|  | 150 | 50% | 32% |
|  | 413 | 17.5% | 1.9% |
| (4) | 0 | 17% | — |
|  | 7 | 17% | — |
|  | 34 | 22% | 12% |
|  | 63 | 3.8% | 2.1% |
|  | 75 | 24% | 11% |
|  | 90 | 16% | 7% |
|  | 105 | 8% | 8% |
|  | 368 | 3.0% | 0.0% |
|  | 399 | 11.9% | 6.8% |
|  | *409 | 60% | 58% |
| (5) | 0 | 5% | 2% |
|  | 14 | 4% | 1% |
|  | 16 | 6.5% | 3.4% |
|  | 46 | 13% | 7% |
|  | 59 | 4.4% | 2.3% |
|  | 74 | 8.1% | 4.2% |
|  | 133 | 28% | 18% |
|  | *444 | 34.6% | 29% |

*See text for description of change in treatment from Solution I to Solution II.

The results indicated in Tables 2, 3, and 4 demonstrate that these patients were effectively treated and that their symptoms of AIDS/ARC are effectively under control as exemplified by a decreased incidence of night sweats, weight loss, lethargy, opportunistic infections and enlarged lymph nodes. Laboratory parameters show a slow return towards normal of NK activity, $T_4$ numbers, and $T_4$:$T_8$ ratios. Furthermore, all patients are able now to work full time or to split time between work and college classes.

The effectiveness of treatment of malignant neoplasms, feline leukemia, and AIDS with gonadotropins may be explained in a number of ways. The rapidity of the response achieved according to the present invention, even with administration of HCG alone as in Example 3, suggests that the present invention is not operating merely by the initiation of a humoral immune response. One explanation is that the low dosage of gonadotropin stimulates a contrasuppression reaction by tipping the balance of the $T_H/T_S$ ratio in favor of activation of $T_H$ cells, and that this leads to the release of a pre-existing immune response (including a CMI response) against the disease. Another explanation may be that the gonadotropin acts in a negative feedback mechanism to turn off production of gonadotropin-like molecules by the malignant cells, leading in turn to a change in the surface charge from the negative charge associated with gonadotropin-like molecules to a more positive charge which facilitates ingestion by macrophages, or leading to exposure of otherwise hidden tumor antigens. However, it is not intended that the present invention be limited to any explanation.

While the present invention has been described in terms of specific methods and compositions, it is understood that variations and modifications will occur to those skilled in the art upon consideration of the present invention.

For example, it is envisioned that various derivatives and fragments of the recited human chorionic gonadotropin and other tumor- or viral-specific antigens will be effective according to the present invention. In addition, although the preferred route of administration is by subcutaneous injection, it is not intended to preclude intramuscular, intraperitoneal, or intravenous injection, intranasal administration, or any other effective route of administration from being included within the scope of the present invention.

Also, inasmuch as other tumor markers, such as carcinoembryonic antigen, alpha-fetoprotein and tissue polypeptide antigen, are classified with HCG in relation to appearance in association with malignant neoplasms and are, therefore, likely to be similarly effective, it is intended that these substances be included within the scope of the present invention as well.

Furthermore, human chorionic gonadotropin, follicle-stimulating hormone, luteinizing hormone and thyroid-stimulating hormone are each glycoproteins composed of an $\alpha$ and a $\beta$ subunit. The $\alpha$ subunit of HCG differs only slightly from an $\alpha$ subunit which is identical in each of FSH, LH and TSH. Although the significance of the subunit structure is yet to be determined, both $\alpha$- and $\beta$-HCG have been associated with tumors. See Acevedo, et al., *Infection and Immunity*, 31:487–494 (1981). Accordingly, it is intended that these pituitary hormones be included within the scope of the present invention.

Still further, it is envisioned that immune enhancers other than lysates of *S. aureus* are believed to be effective. Such other immune enhancers include, for example, BCG mycobacteria, *Corynebacterium parvum* and levamizole. It is accordingly intended that these immune enhancers be included within the scope of the invention.

Additionally, influenza virus vaccines, other than an influenza virus vaccine such as Fluogen TM, are believed to be effective. Such other influenza vaccines include the components of the influenza virus vaccine: neuraminidase and hemagglutinin. It is accordingly intended that such influenza vaccines be included within the scope of the present invention.

In addition, although phenolated saline is described as the diluent used, other diluents such as water, normal saline, physiological saline or any other diluent suitable for administration by the intended route is included within the scope of the invention.

It is anticipated that effective fractionated inactivated fragments of other viruses, related to HIV virus, such as might be present in other retrovirus disease states, e.g., leukemia viruses, HTLV-I, HTLV-II and HTLV-IV viruses, are believed to be effective in alleviating symptoms of those viral disease states. Therefore, it is intended that these are included within the scope of the present invention.

It is contemplated that pharmaceutically effective fragments and effective derivatives of all of the foregoing suggested substances, including those synthesized by recombinant or chemical means by those skilled in the art, may be employed according to the present invention. For example, expression of gene products, i.e., proteins, protein fragments, and peptides have been described for HTLV-III [Chang, et al., *Nature,* 315:151 (1985); Chang, et al., *Bio/Tech.,* 3:905 (1985); Ratner, et al., *Nature,* 313:277 (1985); Crowl, et al., *Cell,* 41:979–986 (1985)]; for HTLV-III/LAV [Muesing, et al., *Nature,* 313:450 (1985); Franchini, et al., *PNAS,* 83:5282–5285 (1986); Putney, et al., *Science,* 234:1392 (1986); and Kieny, et al., *Bio/Tech,* 4:790 (1986)]; and for ARV-2 (AIDS-associated retrovirus) [Luciw, et al., *Nature,* 312:760 (1984); and Sanchez-Pescador, et al., *Science,* 227:482 (1985)]. See also, Hu, et al., *Nature,* 320:537 (1986); Chakrabarti, et al., *Nature,* 320:535 (1986); and Cabradilla, et al., *Bio/Tech,* 4:128 (1986). These effective fragments and derivatives are also intended to come within the scope of the invention as claimed.

Accordingly, it is intended in the appended claims to cover all such equivalent variations which come within the scope of the invention as claimed.

What is claimed is:

1. A method for alleviating symptoms of acquired immune deficiency syndrome in a patient afflicted with acquired immune deficiency syndrome or acquired immune deficiency syndrome related complex comprising the steps of:
    administering to the afflicted patient a member selected from the group consisting of characteristic substances of diseased cells of the acquired immune deficiency syndrome and effective fragments and effective derivatives thereof in a pharmaceutically effective amount which is less than the lowest amount necessary to provoke a humoral immune response in combination with the member, as exemplified by the presence of a positive wheal upon subcutaneous administration; and
    co-administering an immune enhancer in a pharmaceutically effective amount which is less than the lowest amount of the substance necessary to induce a humoral immune response in combination with the member, as exemplified by the presence of a positive wheal upon subcutaneous administration.

2. A method for alleviating symptoms of acquired immune deficiency syndrome in a patient afflicted with acquired immune deficiency syndrome or acquired immune deficiency syndrome related complex comprising the steps of:
    administering to the afflicted patient a member selected from the group consisting of characteristic substances of diseased cells of the acquired immune deficiency syndrome and effective fragments and effective derivatives thereof in a pharmaceutically effective amount which is less than the lowest amount necessary to provoke a humoral immune response in combination with the member, as exemplified by the presence of a positive wheal upon subcutaneous administration; and
    co-administering a bacterial lysate in a pharmaceutically effective amount which is less than the lowest amount necessary to provoke a humoral immune response in combination with the member, as exemplified by the presence of a positive wheal upon subcutaneous administration; and
    co-administering influenza virus vaccine in a pharmaceutically effective amount which is less than the lowest amount necessary to provoke a humoral immune response in combination with the member, as exemplified by the presence of a positive wheal upon subcutaneous administration; and
    co-administering human chorionic gonadotropin in a pharmaceutically effective amount which is less than the lowest amount necessary to provoke a humoral immune response in combination with the member, as exemplified by the presence of a positive wheal upon subcutaneous administration.

3. The method for alleviating symptoms of acquired immune deficiency syndrome as recited in claim 2 wherein said bacterial lysate is a lysate of *Staphylococcus aureus.*

4. The method for alleviating symptoms of acquired immune deficiency syndrome as recited in claim 2, wherein
    said member is administered in a 0.5 cc dose;
    said lysate of *Staphylococcus aureus* is administered in a 0.5 cc dose;
    said influenza virus vaccine is administered in a 0.5 cc dose; and
    said human chorionic gonadotropin is administered in a 2 IU dose.

5. The method for alleviating symptoms of acquired immune deficiency syndrome, as recited in claim 2, wherein said effective fragments comprise peptide T.

6. A composition for alleviating symptoms of acquired immune deficiency syndrome in a patient afflicted with acquired immune deficiency syndrome or acquired immune deficiency syndrome related complex comprising:
    a member selected from the group consisting of characteristic substances of diseased cells of the acquired immune deficiency syndrome and effective fragments and effective derivatives thereof in a pharmaceutically effective amount which is less than the lowest amount necessary to provoke a humoral immune response in combination with the member, as exemplified by the presence of a positive wheal upon subcutaneous administration; and
    an immune enhancer in a pharmaceutically effective amount which is less than the lowest amount necessary to provoke a humoral immune response in combination with the member, as exemplified by the presence of a positive wheal upon subcutaneous administration.

7. A composition for alleviating symptoms of acquired immune deficiency syndrome in a patient afflicted with acquired immune deficiency syndrome or acquired immune deficiency syndrome related complex comprising:
    a member selected from the group consisting of characteristic substances of diseased cells of the acquired immune deficiency syndrome and effective fragments and effective derivatives thereof in a pharmaceutically effective amount which is less than the lowest amount necessary to provoke a humoral immune response in combination with the member, as exemplified by the presence of a positive wheal upon subcutaneous administration; and
    a bacterial lysate in a pharmaceutically effective amount which is less than the lowest amount necessary to provoke a humoral immune response in combination with the member, as exemplified by the presence of a positive wheal upon subcutaneous administration; and influenza virus vaccine in a pharmaceutically effective amount which is less than the lowest amount necessary to provoke a humoral immune response in combination with the member, as exemplified by the presence of a positive wheal upon subcutaneous administration; and human chorionic gonadotropin in a pharmaceutically effective amount which is less than the lowest amount necessary to provoke a humoral immune response in combination with the member, as exemplified by the presence of a positive wheal upon subcutaneous administration.

8. The composition for alleviating symptoms of acquired immune deficiency syndrome, as recited in claim 7, wherein said effective fragments comprise peptide T.

9. The composition for alleviating symptoms of acquired immune deficiency syndrome, as recited in claim 7, wherein said bacterial lysate is a lysate of *Staphylococcus aureus*.

10. The composition for alleviating symptoms of acquired immune deficiency syndrome, as recited in claim 7, comprising:
- a 0.05 cc dose of said member;
- a 0.2 cc dose of said bacterial lysate;
- a 0.05 cc dose of said influenza virus vaccine; and
- a 2.0 International Unit dose of said human chorionic gonadotropin.

* * * * *